(12) United States Patent
Trees et al.

(10) Patent No.: US 11,842,810 B1
(45) Date of Patent: Dec. 12, 2023

(54) REAL-TIME FEEDBACK SYSTEMS FOR TRACKING BEHAVIOR CHANGE

(71) Applicant: Agathos, Inc., San Francisco, CA (US)

(72) Inventors: Andrew Trees, San Francisco, CA (US); Steven Waye, San Francisco, CA (US); Terence Ensworth McDonnell, San Francisco, CA (US); Michael Hoch, San Francisco, CA (US)

(73) Assignee: AGATHOS, INC., San Francisco, CA (US)

(*) Notice: Subject to any disclaimer, the term of this patent is extended or adjusted under 35 U.S.C. 154(b) by 158 days.

(21) Appl. No.: 16/915,216

(22) Filed: Jun. 29, 2020

Related U.S. Application Data

(63) Continuation-in-part of application No. 15/881,642, filed on Jan. 26, 2018, now abandoned, and a
(Continued)

(51) Int. Cl.
*G16H 40/20* (2018.01)
*G06Q 10/0639* (2023.01)
(Continued)

(52) U.S. Cl.
CPC ........... *G16H 40/20* (2018.01); *G06F 3/0482* (2013.01); *G06Q 10/06393* (2013.01);
(Continued)

(58) Field of Classification Search
None
See application file for complete search history.

(56) References Cited

U.S. PATENT DOCUMENTS

| | | | |
|---|---|---|---|
| 2013/0197922 A1 | 8/2013 | Vesto | |
| 2014/0149132 A1* | 5/2014 | DeHaan | G16H 70/20 705/2 |

(Continued)

FOREIGN PATENT DOCUMENTS

| | | | | |
|---|---|---|---|---|
| WO | WO-2013033655 A1 * | 3/2013 | | G06Q 10/10 |
| WO | WO-2017112851 A1 | 6/2017 | | |

OTHER PUBLICATIONS

Volker Tresp et al., Going Digital: A Survey on Digitalization and Large-Scale Data Analytics in Healthcare, Nov. 2016, Proceedings of the IEEE | vol. 104, No. 11 (Year: 2016).*

(Continued)

*Primary Examiner* — Shelby A Turner
*Assistant Examiner* — Matthew H Divelbiss
(74) *Attorney, Agent, or Firm* — Wilson Sonsini Goodrich & Rosati

(57) ABSTRACT

A system is provided for providing real-time actionable feedback. The system comprises: a server in communication with a plurality of client devices, which server comprises a first module configured to process clinical care data using a machine learning algorithm trained model to identify: (i) performance metrics that impact a clinical care outcome in a selected field, and (ii) one or more actions that influence the performance metrics and are actionable to a selected clinical care provider; a second module for generating a real-time measurement of the one or more performance metrics of the selected clinical care provider; and a third module configured to dynamically display on the graphical user interface of a client device of the selected clinical care provider: (i) the real-time measurement of the one or more performance metrics of the selected clinical care provider, and (ii) an adjustment of the one or more actions.

13 Claims, 10 Drawing Sheets

Related U.S. Application Data continuation-in-part of application No. 16/001,179, filed on Jun. 6, 2018, now abandoned, which is a continuation-in-part of application No. 15/881,642, filed on Jan. 26, 2018, now abandoned.

(60) Provisional application No. 62/451,049, filed on Jan. 26, 2017.

(51) Int. Cl.
    *G16H 50/70* (2018.01)
    *G06F 3/0482* (2013.01)
    *H04L 67/01* (2022.01)

(52) U.S. Cl.
    CPC . *G06Q 10/06395* (2013.01); *G06Q 10/06398* (2013.01); *G16H 50/70* (2018.01); *H04L 67/01* (2022.05)

(56) References Cited

U.S. PATENT DOCUMENTS

| | | | |
|---|---|---|---|
| 2016/0092641 A1* | 3/2016 | Delaney | G16H 40/20 |
| | | | 705/3 |
| 2016/0098533 A1 | 4/2016 | Jackson et al. | |
| 2016/0283886 A1 | 9/2016 | D'Amore | |
| 2017/0006135 A1* | 1/2017 | Siebel | G06Q 10/06 |

OTHER PUBLICATIONS

Co-pending U.S. Appl. No. 15/881,642, filed Jan. 26, 2018.
Co-pending U.S. Appl. No. 16/001,179, filed Jun. 6, 2018.
Fischer et al. Is the readmission rate a valid quality indicator? A review of the evidence. Plos one, 9(11) e112282. doi:10.1371/journal.pone.0112282 (Year: 2014).
U.S. Appl. No. 15/881,642 Office Action dated Apr. 17, 2020.
U.S. Appl. No. 15/881,642 Office Action dated Jan. 8, 2020.
U.S. Appl. No. 16/001,179 Office Action dated Apr. 17, 2020.

* cited by examiner

REAL-TIME FEEDBACK SYSTEMS FOR TRACKING BEHAVIOR CHANGE

BACKGROUND

Providing high-value patient care and reducing clinical and practice economic variation are goals for hospital physicians. However, current clinical decision support, analytics, and reporting tools are not sufficient. For instance, shared patients and data limitations impede credible performance metrics and variation analysis. Attribution that is "all-or-nothing" does not reflect the spectrum of influence across care teams or individual physicians. Traditional metrics insufficiently adjust for factors outside physician control. Thus, physicians are either improperly evaluated and/or miss out on helpful feedback. Medical directors and other physician leaders lack the tools to foster physician buy-in and individual behavior change. Under these circumstances, hospitalists usually face frustrating situations, including but not limited to inability to receive immediate and actionable feedback, accidently discharging high-risk patients (e.g., those with congestive heart failure) without follow up, having high length-of-stay cases attributed to them unfairly or without understanding what they could have done differently, not being able to discover their unique practice patterns, and failure to discover why a patient was readmitted.

SUMMARY

A system for behavior tracking and management can overcome the abovementioned insufficiencies. Systems of the present disclosure may be capable of identifying key metrics having impact on a clinical health outcome and generating real-time actionable feedback to a physician for behavior change and management. The real-time actionable feedback may include actions suggested to a physician that may not be outwardly visible by viewing the conventional performance metrics. For instance, the system may allow the hospitalists to receive text notifications, inform patients' care managers, review discharge and handoff notes, and achieve lower length of stay on cases after adjusting for case-mix index. The system may be a health economics and health informatics platform that helps hospitals and medical groups drive higher quality, better outcomes, and lower costs. The system may further track individual and group performance on quality and cost, empower physicians with personalized and actionable feedback on performance, and identify patterns that drive outcomes. For example, the system may automatically produce suggested adjustment based on an update of the data associated with a group of physicians, and an adherence level of the physician in response to receiving the insight, or the behavior change of the physician tracked by the system thereby better engaging physicians into the progress. Features of the system may include analytics engines that provide real-time quality, utilization, and clinical outcome indicators; deep dives that indicate progress over time, peer comparisons, case details, sources and methodologies; and a performance level generator that demonstrates patterns, trends, and associations mapped to metrics and cases.

In an aspect of the present disclosure, a system is provided for providing real-time actionable feedback. The system comprises: a server in communication with a plurality of client devices, which server comprises a first module configured to process clinical care data using a machine learning algorithm trained model to identify: (i) one or more performance metrics that impact a clinical care outcome in a selected field, and (ii) one or more actions that influence the one or more performance metrics and are actionable to a selected clinical care provider; a second module for generating a real-time measurement of the one or more performance metrics of the selected clinical care provider by computing a variation of the one or more performance metrics of the selected clinical care provider relative to the one or more performance metrics of a group of clinical care providers; and a third module configured to dynamically display on the graphical user interface of a client device of the selected clinical care provider: (i) the real-time measurement of the one or more performance metrics of the selected clinical care provider, and (ii) an adjustment of the one or more actions generated based on the real-time measurement, thereby improving the clinical care outcome of the selected clinical care provider.

In some embodiments, the server comprises (i) a first module for identifying one or more performance metrics that impact a clinical care outcome in a selected field, and one or more actions affecting at least one of the one or more performance metrics, wherein the one or more performance metrics are mined from clinical care data; (ii) a second module for generating a real-time measurement of the one or more performance metrics of a clinical care provider by computing a variation of the one or more performance metrics of the clinical care provider relative to the one or more performance metrics of a group of clinical care providers; and (iii) a third module configured to dynamically display: (i) the real-time measurement and (ii) an adjustment of the one or more actions generated based on the real-time measurement on the graphical user interface, thereby improving the clinical care outcome of the associated clinical care provider.

In another aspect, a method for performance tracking and displaying information relating to actions for improving the performance on a graphical user interface is provided. The method may comprise: identifying, by mining from clinical care data, one or more performance metrics that impact a clinical care outcome in a selected field, and one or more actions affecting at least one of the one or more performance metrics; generating a real-time measurement of the one or more performance metrics of a clinical care provider by computing a variation of the one or more performance metrics of the clinical care provider relative to the one or more performance metrics of a group of clinical care providers in the selected field; automatically generating an adjustment of the one or more actions based on the real-time measurement; and dynamically displaying the real-time measurement and the adjustment of the one or more actions to the clinical care provider on the graphical user interface thereby improving the clinical care outcome.

In some embodiments, the one or more performance metrics comprise at least one of cost and quality. In some embodiments, the one or more actions are identified using an algorithm for determining a relevancy of the one or more actions to the clinical care outcome. In some cases, the algorithm is configured to identify an attribution of a given action. In some embodiments, the one or more actions are identified using machine learning methods. In some embodiments, the adjustment of the one or more actions is dynamically calculated based on tracked behavior of the clinical care provider. In some embodiments, the one or more performance metrics in the selected field are different from one or more performance metrics in a different field.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
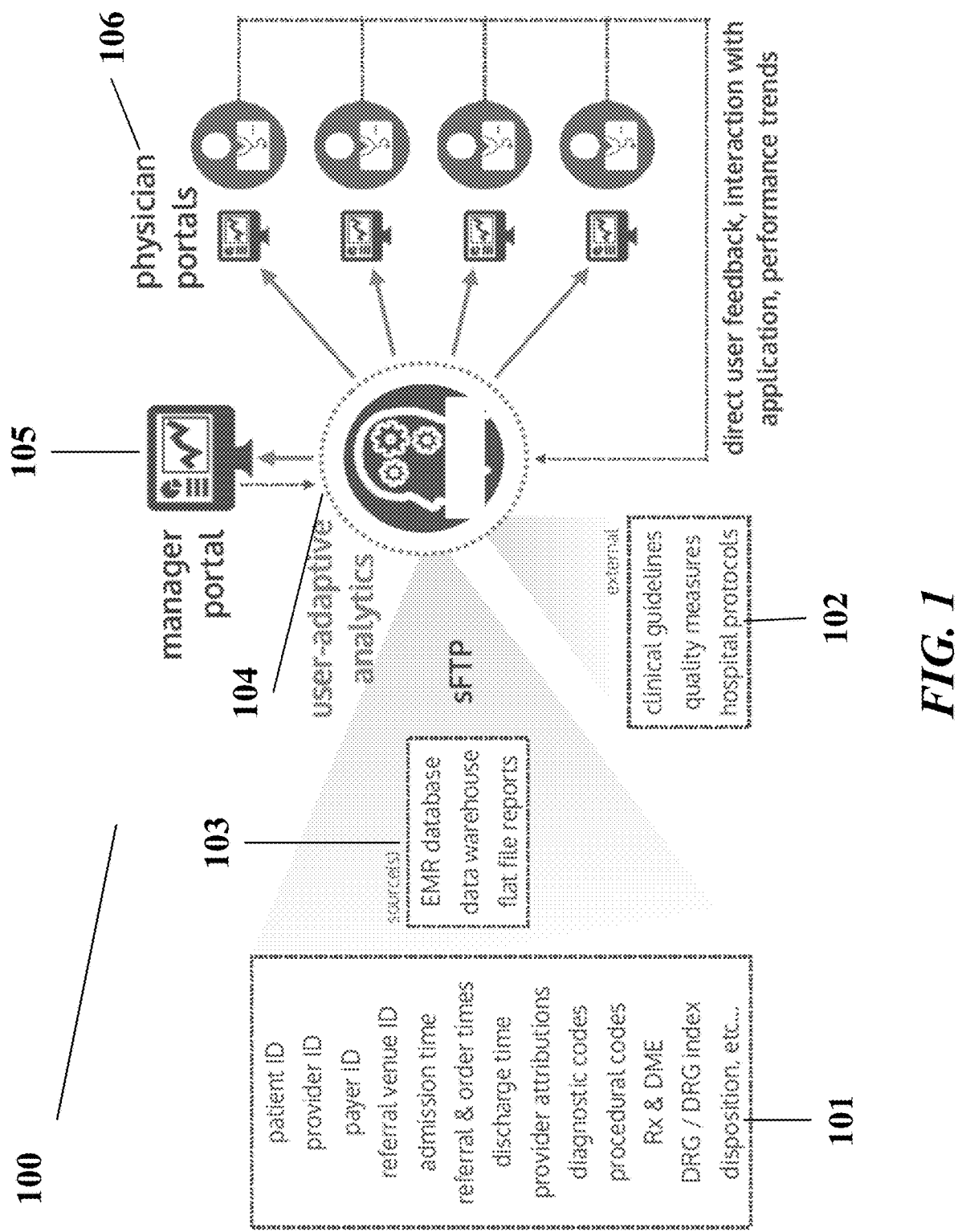
FIG. 1 shows an example of a flow of data through a system for clinical care performance tracking and management.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Systems and methods for clinical care performance tracking and management are provided. Systems as described herein may assist in improving health care outcomes by analyzing and tracking physician or care provider's performance. The system may be configured to identify key metrics that may influence a clinical care outcome. The key metrics may be identified by extracting one or more factors that correlate with health care outcome using data collected from multiple data sources. In some embodiments, the key metrics of a care provider or physician may be quantified by normalizing standard value-based metrics for each key metric. The collected data may be further analyzed along with the key metrics to identify one or more action that impact the key metrics and are executable by a care provider. The provided systems may provide insight to the care provider for adjusting the one or more action in order to move the key metrics to result in an optimized/improved clinical outcome. In some cases, such adjustment may be determined using quantitative analysis. In some cases, the one or more action may be identified and/or an adjustment of the one or more action may be determined using machine learning technologies or other suitable analysis techniques. In some cases, the adjustment of the one or more action may be determined and provided by the system in real-time such that the suggested adjustment may be changed over time. For example, the suggested adjustment may be changed based on an update of the data associated with a group of physicians, an adherence level of the physician in response to receiving the insight, or the behavior change of the physician tracked by the system.

In the discussion that follows, the key metrics may include, but are not limited to: length of stay with respect to different patient groups, overall length of stay, readmission rate with respect to different patient groups, overall readmission rate, geometric length of stay, 30-day readmissions, mortality, HACs, utilization, HEDIS measures, MACRA/MIPS, protocol (a.k.a. "pathway") adherence, CMS core compliance, and/or patient satisfaction. Any of these metrics, or others, may be further enhanced to improve health care outcomes and better track physician or care provider performance by weighting actions and clinical outcomes contributing to the key metrics based on the influence of individual care providers or groups of providers on contributing actions and clinical outcomes, as determined using machine learning technologies or other suitable analysis techniques. The key metrics may be referred to as performance metrics or performance indicators which are interchangeably used throughout this specification. The performance indicators may be organized and stored in a library. For instance, the performance indicators with respect to an individual, a group, an organization may be stored in the library.

In some cases, a system for clinical care performance tracking and management ("system") may support industrial standards. The industrial standards may be TCP/IP connections, API integration, or secure FTP. A data model of the system may comprise data sourced from custom EHR databases and virtual data warehouses. The system may set up a recurring data feed with HL7 and ETL expertise in-house. The recurring data feed may be set up during a period of time. The period of time may be half a day, a day, two days, five days, a week, or longer. The system may use proprietary processes to keep data stable and organized.

The system may allow a user to gain a return on investment (ROI) of 1, 2, 3, 4, 5, 10, or greater. The system may enable hospitals and health systems to achieve higher revenue, operational efficiencies, and reduced utilization. The system may reduce a single hospital physician's or group of hospital physicians' length of stay, a hospital physician's or group of hospital physicians' readmission rate, or otherwise improve performance of a hospital physician or group of hospital physicians' performance on an alternate metric of care quality. The system may further help the care provider, physician leaders, and hospital administrators to monitor, quantify, and improve the value of his/her service. The system may also position and differentiate the value of the service in negotiations with hospitals, health systems, payers, and other third-party providers.

The system may comprise a data warehouse and analytics. The data warehouse and analytics may be designed to conform to the user's needs while leveraging the scale and statistical power of a network. The system may comprise in-house experts experienced with data, performance analysis, practice economics, and management change. The system may help the user determine where to focus his/her efforts. The system may comprise algorithms that may continually calculate default rankings. The system may comprise a unique design and user-adaptive analytics that give physicians precise and properly contextualized metrics.

The user of the system may be a physician, a hospital administrator, or any individual, organization or group in the health system. For example, the users may access a user device or a web account using an application programmable interface (API) provided by the system. In some cases, personal permission to access information provided by the system may be required. This may beneficially allow a user to access insight, performance measurements and the like private to the user. A user may be associated with one or more user devices. Alternatively or in addition, a user device may be associated with one or more users. In an example, if more than one user can be associated with a user device, the software or applications provided by the system can require a user to identify the user by inputting user credentials (e.g., login username, password, PIN, fingerprint, etc.). In another example, if more than one user device can be associated with a user, a user may have a first user device (e.g., mobile phone) and a second user device (e.g., desktop computer) associated with the user at any point in time. The users may be located geographically at a same location, such as users working in a same office or a same geographical location. In some instances, some or all of the users and user devices may be at remote geographical locations (e.g., different cities, countries, etc.), although this is not a limitation of the invention.

The system may be implemented by providing a webpage, application, program, or any appropriate software. In some cases, the system may comprise a web application. An access to the web application may not be linked to any clinical encounters or workday processes. The system may allow the user to login and review cases retrospectively. The system may also allow the user to gain action items, reminders, and takeaways for future clinical work. The system may adopt an approach that relieves click fatigue, saves time, and produces more attentive clinical decision making and higher physician and patient satisfaction. The system may notify the user with updates and performance levels of particular relevance or timeliness.

The system may comprise a plurality of client devices. Each individual client device is configured to display a user interface associated with a clinical care provider. The system may further comprise a server in communication with the plurality of client devices. The server may comprise a first module for identifying one or more performance metrics that impact a clinical care outcome, wherein the one or more performance metrics are mined from real-time clinical care data. The one or more performance metrics may be mined from real-time clinical care data. The server may comprise a second module for generating a measurement of the one or more performance metrics of an associated clinical care provider. The measurement may be generated by computing a variation of the one or more performance metrics compared to the one or more performance metrics of a group of clinical care providers. The one or more performance metrics may include, but not limited to, geometric length of stay, 30-day readmissions, mortality, HACs, utilization, HEDIS measures, MACRA/MIPS, protocol adherence, CMS core compliance, patient satisfaction, and/or any of the aforementioned calculated based on actions and clinical outcomes weighted based on the influence of individual care providers or groups of providers on contributing actions and clinical outcomes. The server may comprise a third module for generating a possible adjustment of one or more actions based on the measurement thereby improving a clinical care outcome. The one or more actions may be identified using an algorithm for determining a relevancy of the one or more actions to the clinical care outcome, and wherein the adjustment of the one or more actions are provided to the clinical care provider on the associated user interface.

Data Processing and Multiple Data Sources

The system may capture data from one or more sources, determine one or more performance metrics that impact a clinical care outcome, and quantitatively analyze the one or more performance metrics by calculations and machine learning. The data may be real-time clinical data. The system may aggregate the data from clinical care providers ("providers"). The providers may include hospitalists, administrators, or any individuals, groups or organizations in the healthcare industry. The providers may or may not be the users of the system.

The data may be gathered from one or more sources. The one or more sources may include, but not limited to, Centers for Medicare & Medicaid Services ("CMS"), hospitals, health systems, health plans and various others. Various other sources may be utilized such as patients' personal health care tracking data (e.g., wearable device, home medical device data, etc). The data gathered may be in various forms such as Electronic Health Records, Visit Scheduling information, Lab and Diagnostic reports, Pharmacy data, or a patient's own health tracking data.

After gathering the data, the system may create a mechanism surrounding the collection and maintenance of the data. The mechanism may ingest the data into a computing device on a recurring basis automatically. The data may be replicated and/or be available on a database. The data may then be presented on a portal of the database. The data may be pulled from the database by Extract, Transform, and Load (ETL) functions. The data may be stored in table hierarchies pulled from the database before being posted to the portal. The data may be checked to ensure it is up to date. The data may be easily searchable and understood. The data may be edited by the system when new information of providers or users emerge. The data may be delivered to different users at the same time.

They system may perform analytics on the data to generate one or more performance metrics. The performance metrics may be the factors that impact a clinical outcome. The performance metrics may be identified by analyzing a correlation between the performance metrics and the clinical outcome. In some cases, the performance metrics may be determined based on user input received by the system indicating an interest of performance metrics to be measured. For example, a user interface may be provided allowing the user to select performance metrics or desired outcome from a menu of options. Alternatively or additionally, the performance metrics may be identified by mining the health data. For example, the performance metrics may be identified using machine learning methods (e.g., unsupervised machine learning) or clustering techniques. The one or more performance metrics may include, but not limited to, geometric length of stay, 30-day readmissions, mortality, HACs, utilization, HEDIS measures, MACRA/MIPS, protocol adherence, CMS core compliance, patient satisfaction, and/or any of the aforementioned calculated based on actions and clinical outcomes weighted based on the influence of individual care providers or groups of providers on contributing actions and clinical outcomes. The clinical outcomes, in some cases, may be presented by one or more clinical outcome indicators. The clinical outcome indicators may be related to inpatient factors such as cost, or patient factors such as patient's treatment outcome. The utilization of the one or more performance metrics may comprise imaging, consulting, and/or lab experimenting.

The system may be coupled to a data warehouse to power the analytics. The data warehouse may utilize any suitable database techniques. For instance, structured query language (SQL) or "NoSQL" database may be utilized for storing collected health data and generated analytics. The database of the present invention may be implemented using various standard data-structures, such as an array, hash, (linked) list, struct, structured text file (e.g., XML), table, JSON, NOSQL and/or the like. Such data-structures may be stored in memory and/or in (structured) files. In another alternative, an object-oriented database may be used. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the database of the present invention is implemented as a data-structure, the use of the database of the present invention may be integrated into another component such as the component of the present invention. Also, the database may be implemented as a mix of data structures, objects, and relational structures. Databases may be consolidated and/or distributed in variations through standard data processing techniques. Portions of databases, e.g., tables, may be exported and/or imported and thus decentralized and/or integrated. In some embodiments, the system may construct the data warehouse in order to deliver the data to the users efficiently. For example, the system may create new algorithms to extract, transform, and load (ETL) the data. In some embodiments, the system may construct the data warehouse using proprietary database architecture or data structures to provide an efficient database model that is especially adapted to large scale databases, is easily scalable, and has reduced memory requirements in comparison to using other data structures.

In some cases, the system may comprise a component configured to organize the collected data from different providers and/or users and store the parsed/processed data into one or more table hierarchies. The table hierarchies may comprise one or more tables. The table hierarchy may be a tiered structure to store the data. The tiered structure may comprise a top tier, a middle tier and/or a lower tier. The top tier may comprise scores of different users. Different users and/or providers may have different scores. The scores may be specific to a specialty. The data may be normalized in the one or more tables to maximize efficiency and integrity. The tables may include data specific to each user. The data in the tables may be further normalized. Further normalization of the data may include emerging the data from one user with other data from another user.

Calculating Metrics and Derived Data

The system may display the data in a simple format to providers and/or users through an application. The system may determine one or more performances metrics by using one or more programming languages. The one or more programming languages may include Active Server Page (ASP), ActiveX, (ANSI) (Objective-) C (++), C #and/or .NET, Common Gateway Interface (CGI) scripts, dynamic (D) hypertext markup language (HTML), FLASH, Java, JavaScript, Practical Extraction Report Language (PERL), Hypertext Pre-Processor (PHP), pipes, Python, wireless application protocol (WAP), WebObjects. The one or more performance metrics may be presented to users though scores. The scores may show users how their performance metrics compare with the national averages or other specific targets set by each user. The national average scores may be provided by CMS. The scores may be associated with measurement of the users' performance metrics.

The system may help users accomplish different tasks. The different tasks may be understanding to what degree the user is responsible for the variance in a certain metric and discovering which actions the user may take to improve performance. The system may further help users understand how providers affect clinical care outcomes (or "outcomes"). The system may build predictive models that can take a hospital admission and outpatient visit into account. The predictive models may be based on additional factors such as surgical cases or episodes of care. The predictive models may be used to predict the expected outcomes for the higher performing and lower performing providers or users. The expected outcomes may be transformed into one or more parameters such as length of stay or readmissions.

The predictive models may allow the providers or users to attribute ownership of specific actions, cases, visits, admissions, or episodes to other providers or users per their level of influence. In some cases, the predictive models may be used to identify attribution of a given action. For example, the predictive models may be capable of tracking and identifying if an action is taken by a physician, a nurse, administrator, or other providers so as to provide an accurate analysis on the relevancy of actions and outcomes.

FIG. 1 shows an example of a flow of data through the system 100. Data 101 may be extracted from multiple data sources 103. As shown in the example, the parsed or processed data 101 may include patient ID, provider ID, payer ID, referral venue ID, admission time, referral and order time, discharge time, provider attributions, diagnostic codes, procedural codes, Rx and DMA, DRG or DRG index, disposition and the like. The data sources 103 may include EMR database, data warehouse, flat file reports and various others as described elsewhere herein. The sources 103 may be transferred or secured by a secure file transfer protocol ("SFTP") (e.g., SFTP 203 in FIG. 2A). In some cases, external data 102 may also be used for generating insight and/or performance metrics. The external data 102 may comprise clinical guidelines, quality measures, hospital protocols and various others.

The data may be analyzed in a central portal 104 through analytics. The analytics may be a user-adaptive analytics. Results of the analysis may include performance metrics and a measurement/value of the performance metrics. The results may be transferred from the central portal 104 to a manager portal 105. The manager portal 105 may perform further analysis of the results or is configured to modify the user-adaptive analytics. For example, the manager portion 105 may allow a developer or administer to modify one or more parameters of the user-adaptive analytics, a structure of the database, input a command to change a process or operations performed by the user-adaptive analytics and the like. In some cases, the manger portal 105 may transmit the further analysis of the results back to the central portal 104. The central portal 104 may transmit the results to physician portals 106. The physician portals may collect direct user feedback, interaction with application, and performance trends, which may be transferred back to the central portal 104.

Quantitative Analysis of Behavior

The system may provide insight about adjustment of one or more care actions to improve performance metrics through mining the data in the data warehouse. The data may be real-time clinical care data. The clinical care data may be analyzed with respect to performance metrics to identify one or more actions a physician may take in order to improve a clinical outcome. An insight may comprise a quantitative analysis result of the one or more actions of a physician and/or suggested adjustment/change of the one or more actions. In some cases, the insight may also provide reasons of having higher length of stay than peers, unique practice patterns of the users, and reasons why a patient was readmitted and the like. The insight may further include how to improve patient care and how to reduce costs. In some cases, the system may perform analysis on one or more performance metrics at once.

As mentioned above, the system may identify one or more actions from a plurality of potential factors that may influence a performance metric. Examples of potential factors may include, but not limited to, procedure decisions, discharge decisions, time of care, specialty care and consultation, mental health treatment, advanced care planning, patient self-care, medical equipment used, facility safety, and/or prescriptions or pharmaceutical usage and the like.

The procedure decisions may determine if procedures affect outcomes for patients. The discharge decisions may determine if discharge decisions have positive/negative outcomes for patients. The timing of care may show whether when patients receive care and begin treatment is a factor for success to improve outcomes. The specialty care and consultation may determine if consulting physicians with specialist knowledge when treating certain conditions leads to better patient outcomes. The mental health treatment may determine if patients with potential mental conditions are treated if that leads to more positive outcomes. The patient self-care may determine if patients' personal habits surrounding health affect outcomes. The advance care planning may determine if giving patients palliative care or other advanced care planning leads to more positive outcomes. The personal habits may determine whether personal habits, including drinking water, smoking, eating healthy, sleeping, exercise, affect outcomes. The medical equipment used may determine if certain brands of medical equipment are more effective in generating positive patient outcomes than others. The facility safety may determine if certain facility practices and procedures have positive or negative effects on patient outcomes. The prescriptions/pharmaceutical usage may determine if certain drugs and their side effects have positive or negative effects on patient outcomes.

In some embodiments, the system may determine the one or more actions that are influential towards specific outcome or performance metrics by an influence algorithm. The influence algorithm may identify actions then analyze the impact of the identified actions with respect to a specific outcome. In some cases, the influence algorithm may involve using machine learning techniques (e.g., unsupervised learning, clustering methods) to determine a variance of a physician relative to a group of physicians. In some cases, the influence algorithm may utilize a feature selection or a feature extraction technique to assess the impact of different factors on an overall quality of a performance model.

Insights may be personalized with respect to a healthcare organization, hospital, a practice field, a department, a single provider and the like. This provides benefit by targeting different users to increase likelihood of the adjustment of one or more actions. The one or more actions tracked and monitored for different users may be different. The one or more actions may be different across different users, practice field, locations, and the like. In some cases, the one or more actions may be personalized to the target different users to increase likelihood of the adjustment of one or more actions. The action adjustment may be tracked over time at individual user's level. It is noted action adjustment or adjustment also refers to behavior change which are interchangeably used throughout the specification.

Figure 2A:
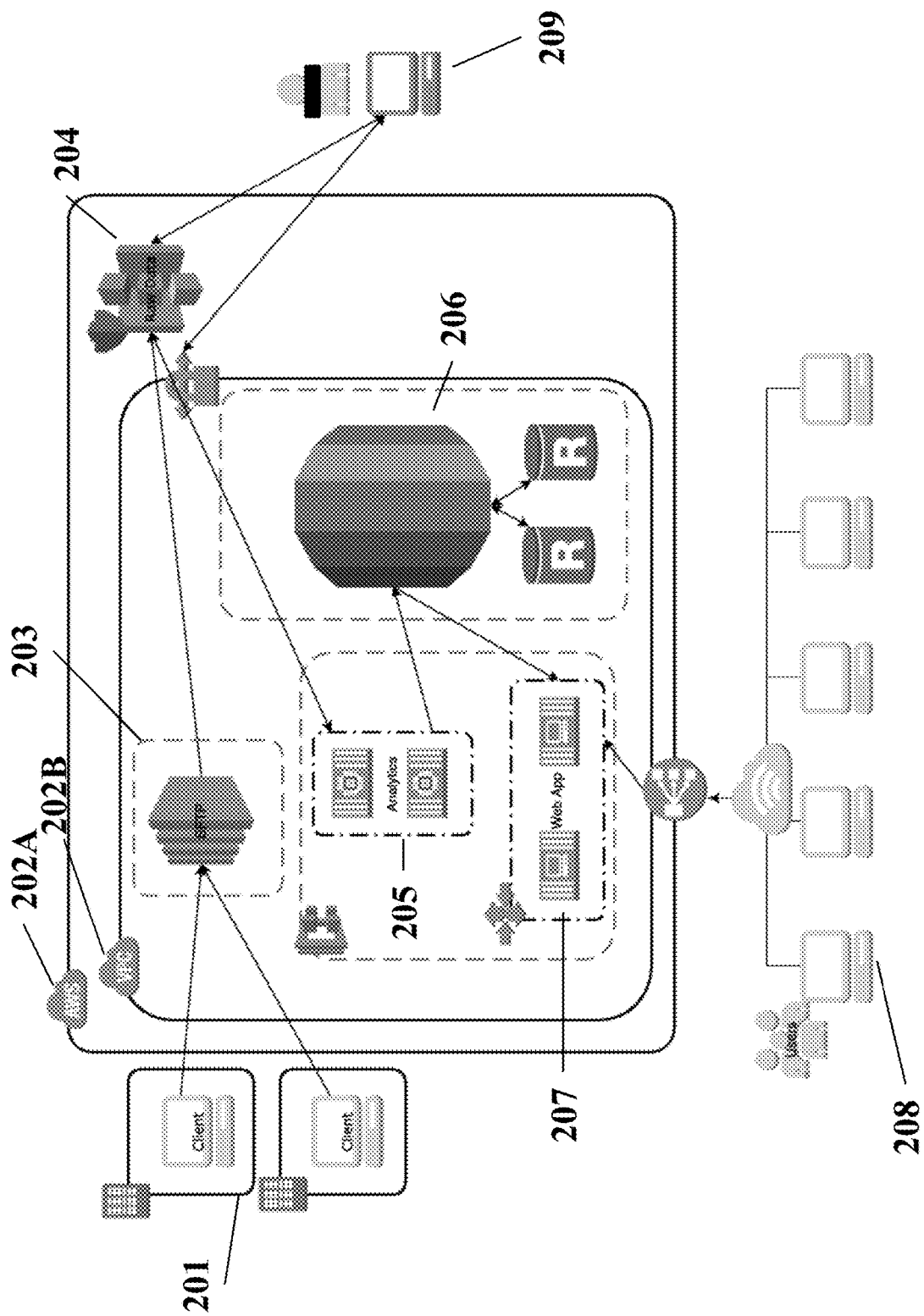
FIGS. 2A-2B show examples of block diagrams of a platform capable of implementing the system.

FIG. 2A shows an example of a block diagram of a platform capable of implementing the system. The data may be collected from the health system(s) 201 and/or directly from providers/other users 202. The data may include patient ID, provider ID, payer ID, referral venue ID, admission time, referral and order time, discharge time, provider attributions, diagnostic codes, procedural codes, Rx and DMA, DRG or DRG index, and/or disposition. The data may be collected and stored in raw format 204. The raw data may be analyzed by an analytics engine 205. The analyzed data may be transferred to 206 and be categorized. The categorized data may include performance levels and performance metrics. The categorized data may be transferred to a web application 207. The web application 207 may be connected to electronic devices.

Figure 2B:
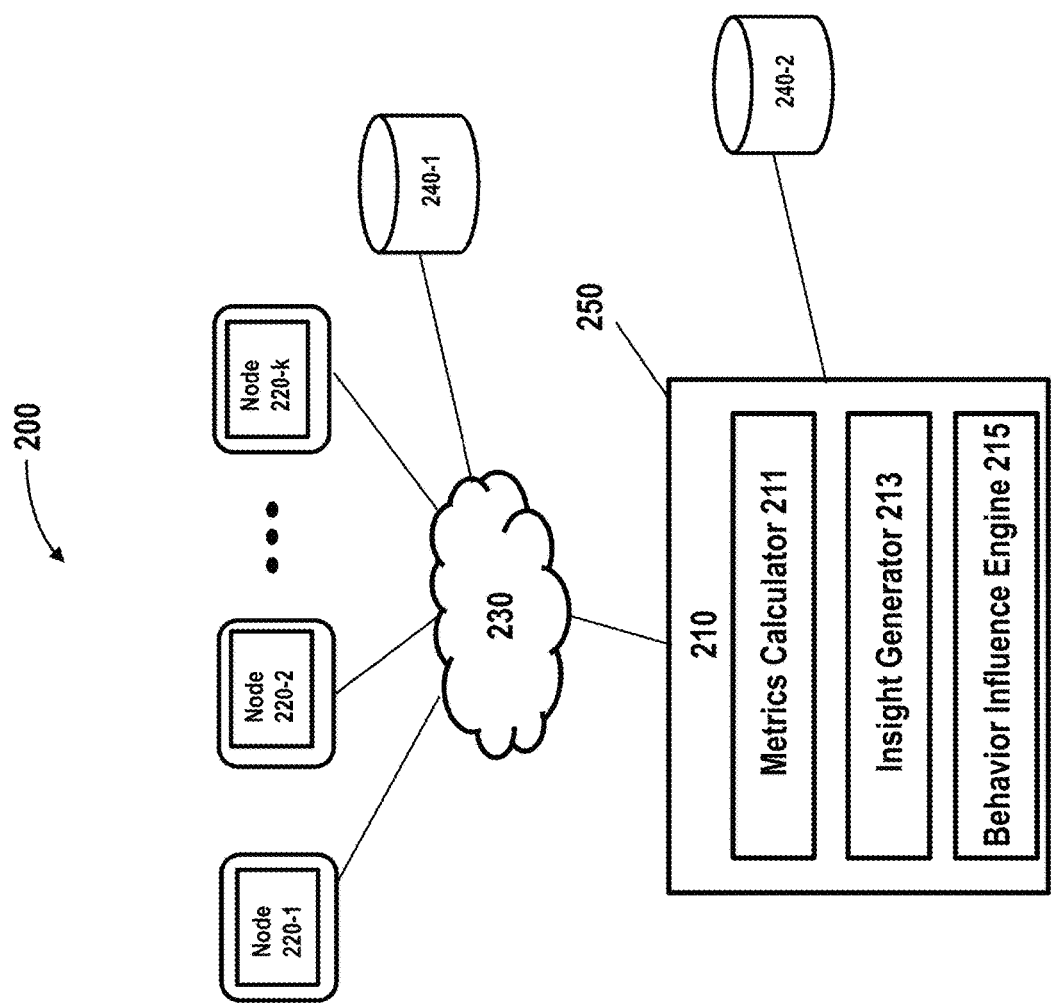

FIG. 2B shows an exemplary network 200 utilized by a system 210 described herein. The network 200 can comprise a plurality of nodes 220-1, 220-2, and 220-k. A node may be a logically independent entity in the network layout. Therefore, the plurality of nodes in the network layout can represent different entities. For example, each node may be associated with a user, a group of users, or groups of users. For example, a node may correspond to an individual entity (e.g., an individual). In another example, a node may correspond to multiple entities (e.g., a group of individuals). A node can be any device (e.g., computer device 208 in FIG. 2A) equipped with communication capabilities, which communication capabilities can be cloud-based. The communications can be wired or wireless communications. The node can be operating over various technologies such as Global System for Mobile communication (GSM), Universal Mobile Telecommunications System (UMTS), High Speed Downlink Packet Access (HSDPA), Code Division Multiple Access (CDMA), Long Term Evolution (LTE), Worldwide Interoperability for Microwave Access (WiMAX) and infrastructure IEEE 802.11 variants, such as IEEE 802.11a/b/g/n/ac, or a cloud-based system, and various others. A node can be a Bluetooth or Wi-Fi enabled device, such as laptops, cellular phones, Personal Digital Assistant (PDA), Smartphone, HSDPA terminal, CSMA terminal and various other access terminals. A node can operate as a broadcast node, relay node, source node, sink node or recipient node in the network. A node can or cannot be mobile, or cloud-based.

A node can be various types of computing devices such as personal computers, tablet computers, smart phones, set top boxes, desktop computers, laptops, gaming systems, servers, data centers, and various other devices or systems. A node can be any type of network devices. The plurality of nodes can establish communications with others devices or systems in the network (e.g., system 210, databases 240-1, 240-2, other third party server, etc). The network 230 can be a wireless network, wired network, a cloud-based network, or any combination thereof. For example, the network can comprise one or more of the Internet, an intranet, a cellular network, a home network, a person area network, etc., through an ISP, cellular, or broadband cable provider, and the like. The network can comprise an internet protocol interfaces, such as one or more network components, data servers, connection nodes, switches, and the like. In some cases, the plurality of nodes can be considered as part of the network. The plurality of nodes can be configured to run any suitable applications for conducting a transaction.

The system 210 may comprise a plurality components or modules configured to perform various functions as described herein. In an example, the system 210 may comprise a metrics calculator 211, an insight generator 213 and a behavior influence engine 215.

The metrics calculator 211 may be configured to process and organize data collected from multiple sources. The processed data may then be analyzed to determine one or more performance metrics using aforementioned methods. For example, the metrics calculator 211 may use predictive model to identify the performance metrics that may influence a clinical outcome. In some cases, the performance metrics may vary across different physician, clinical practice field, organization, location or other disciplines. Performance metrics associated with different fields may be different. For example, the performance metrics associated with a given field may be different from performance metrics associated with a different field. As utilized herein a "field" may refer to a practice field, a group of physicians, an organization, a department and the like. The metrics calculator 211 may then compute a value or generate a measurement for each performance metric associated with the physician. In some cases, the value may be normalized with respect to the performance metrics of a group of physicians.

The insight generator 213 may be configured to generate insight and provide to the care provider for adjusting the one or more actions thereby improving a clinical outcome. In some cases, such adjustment may be determined using quantitative analysis. As described above, the one or more actions may be identified and/or an adjustment of the one or more actions may be determined using machine learning technologies or other suitable analysis techniques. In some cases, a clinical outcome may be influenced by a plurality of actions or performance some of which may not be actionable or applicable to a particular health care provider. Machine learning technologies may be employed to identify the actionable actions personalized to a user that may not be obvious or explicit. In some cases, the one or more actionable actions associated with a physician may be determined using a machine learning algorithm trained predictive model.

In some cases, the adjustment of the one or more actions may be determined and provided by the system in real-time such that the suggested adjustment may vary along with time. The adjustment of the one or more actions may be personalized based on the tracked behavior of a physician. For example, the suggested adjustment may vary or be delivered to a user based on an update of the data across different physicians, an adherence level of the physician in response to receiving the insight, or the behavior change of the physician tracked by the system. In some cases, the adjustment may be determined using a machine learning algorithm trained predictive model.

A predictive model may be a trained model or trained using machine learning algorithm. A machine learning algorithm may be a neural network, for example. Examples of neural networks include a deep neural network, convolutional neural network (CNN), and recurrent neural network (RNN). The machine learning algorithm may comprise one or more of the following: a support vector machine (SVM), a naïve Bayes classification, a linear regression, a quantile regression, a logistic regression, a random forest, a neural network, CNN, RNN, a gradient-boosted classifier or repressor, or another supervised or unsupervised machine learning algorithm.

In some case, a predictive model for identifying the one or more actionable actions associated with a physician may be trained using unsupervised learning algorithm (e.g., generative adversarial network (GAN), Cycle-GAN, clustering analysis, etc.). As an example, the one or more actionable actions may be identified using clustering analysis. The clustering analysis may involve a modified k-means clustering based on an error metric that is other than Euclidean distance. For example, the error metric may include integrated area between a given pair of the Kaplan-Meier estimator curves. The Kaplan-Meier estimator curves may be generated based on the data (e.g., performance metrics or other data described in FIG. 2A) and a set of potential actions. Furthermore, the clustering analysis may involve: expectation maximization clustering and/or density clustering.

In some cases, the clustering analysis involves a range of k values, the clustering analysis may be repeated N times (where N is an integer), and the determined natural groups may have a k value with minimum values of the error metric over the range of k values. Alternatively, prior to performing the clustering analysis, the computer system may receive a user-specified k value.

Additionally, the identified actions may be associated with at least natural groupings having a centroid separation exceeding a threshold value. Thus, the centroid separation may be used to identify the potential actions that are actionable to a physician (i.e., the actionable feedback).

Similarly, the key metrics that impact a clinical care outcome may be identified from a plurality of potential performance metrics using a predictive model. In some case, the predictive model for identifying the key metrics may be trained using unsupervised learning algorithm (e.g., generative adversarial network (GAN), Cycle-GAN, clustering analysis, etc.).

The system 210 may optionally comprise a behavior influence engine 215. The behavior influence engine 215 may be configured to deliver the insight to a user in an optimized fashion. The behavior influence engine 215 may, for example, keep track of a behavior change of the user in real-time and generate notifications or alerts to the user based on the real-time information. The behavior influence engine 215 may be configured to determine when and how a user may adjust the one or more actions in order to optimize a behavior change outcome. Examples of the notifications and messaging system are described with respect to FIGS. 3C-3F.

In some embodiments, the system 210 may be implemented by a server 250. The server may comprise one or more server computers configured to perform one or more operations consistent with disclosed embodiments. In one aspect, a server may be implemented as a single computer through which a user device 220-1, 220-2, and 220-k is able to communicate with other components of the network 230. In some instances, a user device may communicate with the server 250 through the network. In other instances, the server may communicate on behalf of a user device with the one or more systems or the databases through the network. In one aspect, the server may embody the functionality of one or more systems. In another aspect, the one or more systems may be implemented inside and/or outside of the server. For example, the one or more systems may comprise software and/or hardware components included with the server or remote from the server. A server may also be a server in a data network (e.g., a cloud computing network).

The network 230 may be configured to provide communication between various components of the network layout depicted in FIG. 2B. The network 230 may comprise one or more networks that connect devices and/or components in the network layout to allow communication between the devices and/or components. For example, the network may be implemented as the Internet, a wireless network, a wired network, a local area network (LAN), a Wide Area Network (WANs), Bluetooth, Near Field Communication (NFC), or any other type of network that provides communications between one or more components of the network layout. In some embodiments, the network may be implemented using cell and/or pager networks, satellite, licensed radio, or a combination of licensed and unlicensed radio. The network may be wireless, wired (e.g., Ethernet), or a combination thereof.

The server 250 may access and execute the one or more systems to perform one or more processes consistent with the disclosed embodiments. In certain configurations, the one or more systems may be a software stored in memory accessible by the server (e.g., in a memory local to the server or remote memory accessible over a communication link, such as the network). Thus, in certain aspects, the one or more systems may be implemented as one or more computers, as software stored on a memory device accessible by the server, or a combination thereof. For example, one system may be a computer hardware executing one or more data processing techniques, and another system may be software that, when executed by the server, performs one or more user interface techniques.

The node devices 220-1, 220-2, and 220-k, server 250, and the one or more systems 210 may be connected or interconnected to one or more databases 240-1, 240-2. The one or more databases may be one or more memory devices configured to store data as described elsewhere herein. Additionally, the one or more databases may also, in some embodiments, be implemented as a computer system with a storage device. In one aspect, the one or more databases may be used by components of the network layout to perform one or more operations consistent with the disclosed embodiments. In certain embodiments, the one or more the databases may be co-located with the server 250, and/or co-located with one another on the network. One of ordinary skill will recognize that the disclosed embodiments are not limited to the configuration and/or arrangement of the one or more databases.

In some embodiments, the system may pinpoint high impact instances of care variation. The system may further compare the providers against their peers, or connect low performing providers with high performing providers. The system may also provide actionable suggestions on how to improve.

The system may provide performance metrics to users and measure how action might be adjusted. The system may measure patients' outcomes, encourage usage of the product, and measure improvements of the outcomes. The system may utilize machine learning, virtual currencies, and/or evidence based feedback. The machine learning may develop neural network algorithms optimizing for user engagement or performance, particularly concerning which data to show users. The virtual currencies may include gamification tokens, rules engines, and other quasi-economic units influencing user access to content, explicit rewards, perception within an ecosystem, and their actions within and beyond the application. The evidence based feedback may display examples to the users of other providers showing positive outcomes obtained by following recommendations.

The user may adjust his/her one or more actions according to the insight or action measurement that the system generates. The system may educate the users on how their one or more actions affect patients' outcomes. The system may allow users to monitor regularly. The system may provide recommendations that users adhere to. For example, the system may inform the users a prescription of a certain medicine on discharge to a certain subset of patients could achieve a drop of the readmission rate by 15%.

The system may collect feedback from the users to further improve the way to calculate the performance levels and the performance metrics, and optimize the UI. The application may create an increasingly personalized home environment for the users. The system may collect the data and utilize machine learning to incorporate this data into the algorithm to remove irrelevant information. The system may target the information that has the greatest impact and notify the users when there is information of relevance to them and their care patterns. The system then may provide instruction to the users and help them improve over time.

The system may be implemented by way of machine-executable code stored in memory or other electronic storage. Such machine-executable code may be included in an application (or "app"). The application may be executed on an electronic device of a user, such as a desktop. The application may be executed on a mobile electronic device of a user, such as a portable computer or Smart phone (e.g., iPhone). The application may include a user interface, such as a graphical user interface, to provide various functions.

The UI may be configured to display insights to a user according to relevancy or importance. In an example, the UI may display important information first. The UI may display information using a login page organized by metric type. Patient diagnosis may be presented by icons. The icons may be in the shape of square, circle, triangle, etc. An order of the icons may be presented according to which icon is more relevant to physicians. An algorithm may be used to determine the order of the icons. The algorithm may adjust over time based on the action adjustment of the users. The icons may include a score visualization showing real-time scores against targets, incremental improvement (or decline), links to scoring methodology, and links to additional features with more information. The UI may demonstrate one or more features on the screen. The one or more features may include graphical displays of progress over time, peer comparison, case examples, data and evidence repository, and user feedback channel.

FIGS. 3A-D show examples of UIs as part of the application that is executed on the electronic device of the user. The electronic device comprises an electronic display screen ("screen") for presenting the UI.

Figure 3A:
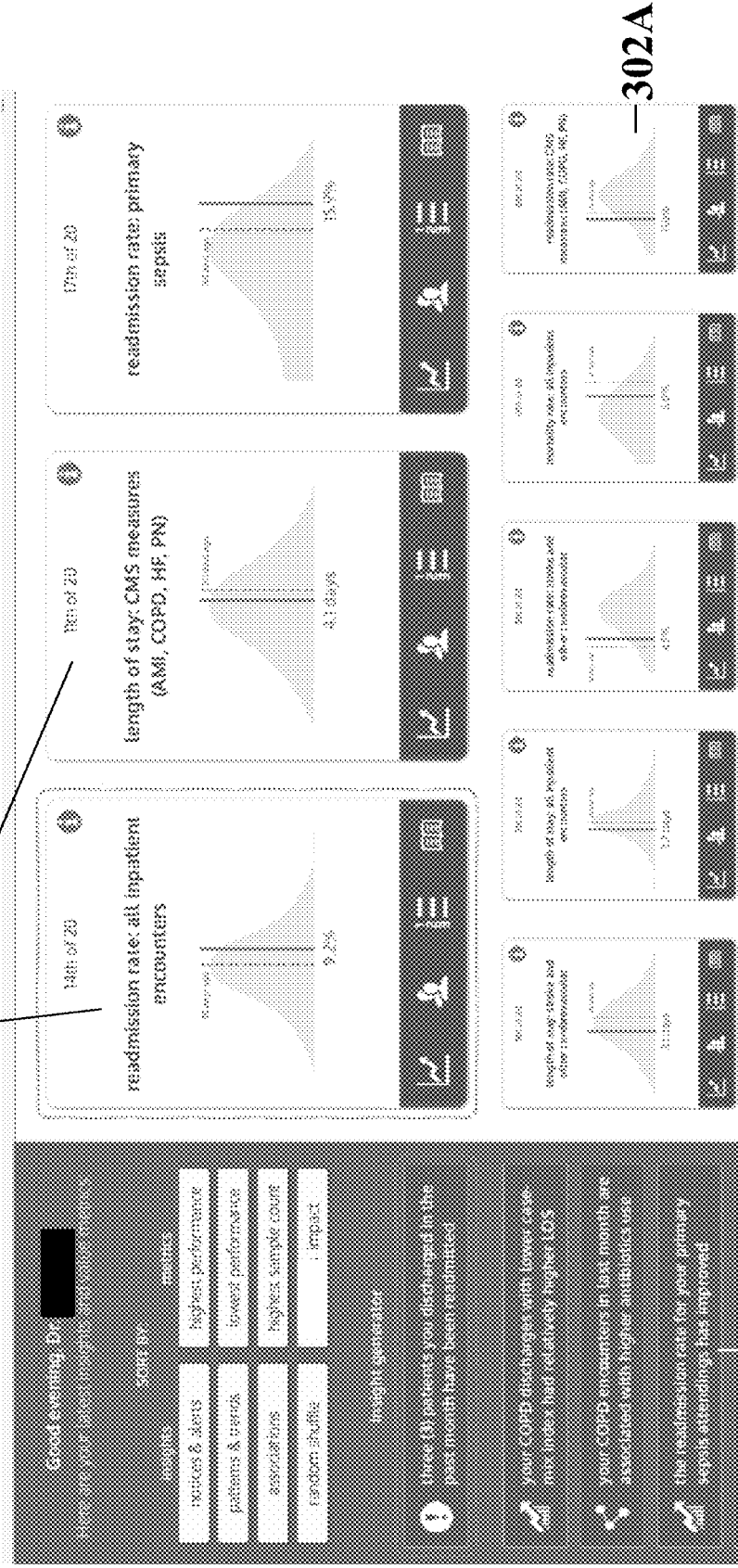
FIGS. 3A-3D show examples of user interfaces (or "UIs") as part of an application of the system that is executed on an electronic device of a user.

With reference to FIG. 3A, the UI comprises a plurality of graphical elements displayed on the screen. The plurality of graphical elements may comprise an information column 301. The information column 301 may show a plurality of horizontal bars. The horizontal bars may allow the user to choose how to visualize the data. The user may either choose to visualize the data by performance levels or performance metrics. If the user chooses to visualize the data by the performance levels, he/she may choose among different options. The different options of the performance levels may include notices and alerts, patterns and trends, associations, and random assortment. If the user chooses to visualize the data by the performance metrics, he/she may choose among different options. The different options for sorting and filtering of the performance metrics may include highest performance, lowest performance, highest sample court, and impact.

The horizontal bars may also provide the user with information related to a performance level generator. The information related to the performance level generator may include how many patients that are discharged by the user in the past month have been readmitted, whether the user's COPD discharges with lower case mix index had relatively higher LOS, whether the user's COPD encounters in a month are associate with higher antibiotics use, and/or whether the readmission rate for the user's primary sepsis attendings has improved. The information column may be positioned at the left side of the screen, in the middle of the screen, or at the right side of the screen.

The plurality of graphical elements may be icons 302. The shape of the icons may be rectangular. The icons may present information related to either the performance levels or performance metrics, depending on the user's choices. The information related to the performance levels and/or the performance metrics may include readmission rate about all inpatient encounters, length of stay measured by CMS, and/or readmission rate about primary sepsis. The information may further comprise a ranking, a distribution figure, or a percentile number. The icons may be positioned at the left side of the screen, in the middle of the screen, or at the right side of the screen.

Figure 3B:
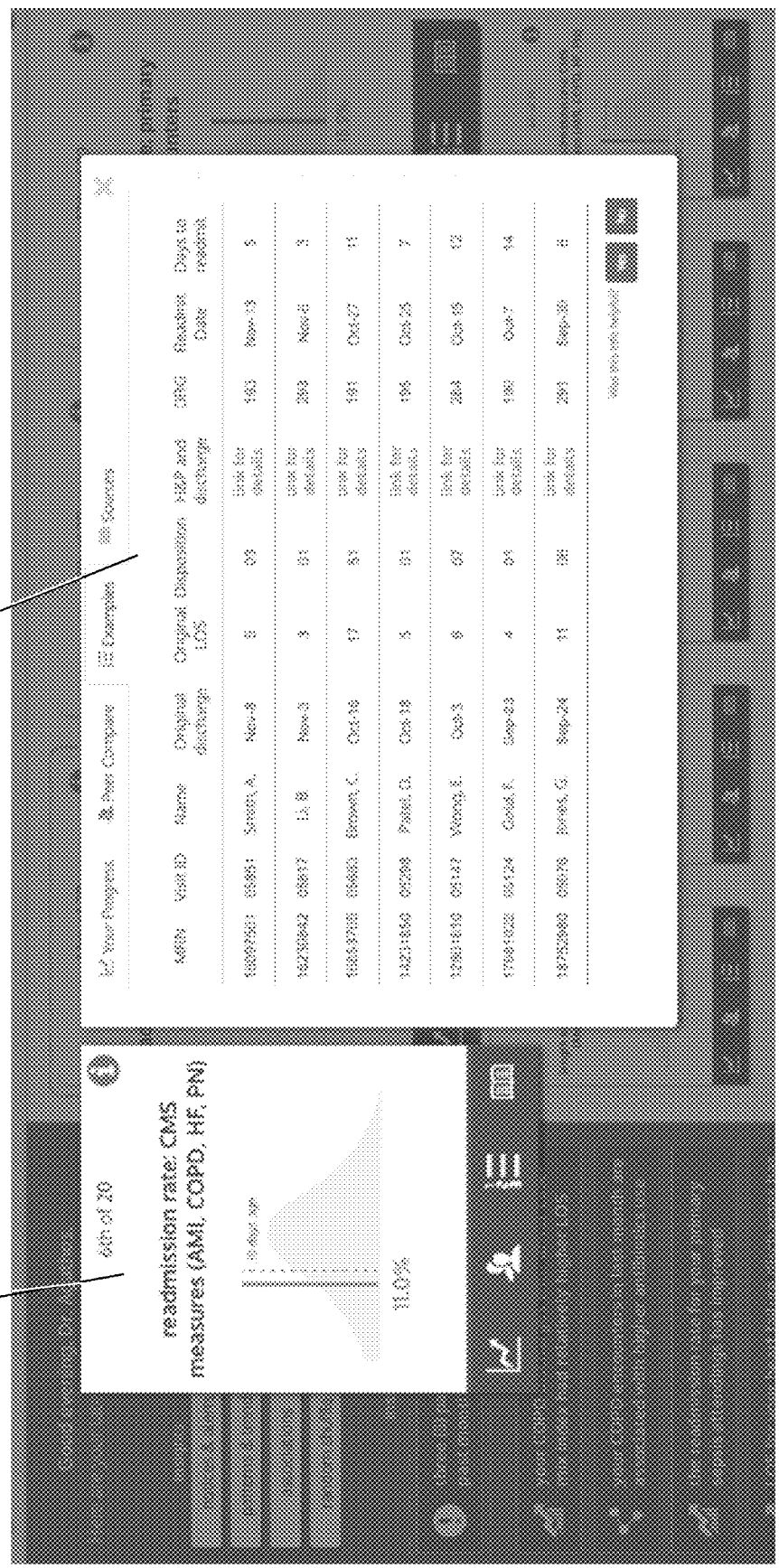

FIG. 3B demonstrates an enlarged view of the icon 302A. The enlarged view may comprise an enlarged icon 302B. The enlarged icon may demonstrate same information as the icon 302A. The same information may comprise a ranking, a distribution figure, and/or a percentile number. The enlarged view may further comprise a table 303 associated with the enlarged icon 302B. The table 303 may demonstrate patients' information. The patients' information may include visit ID, name, original discharge date, original length of stay, disposition, readmission date, and/or days to resident. The patients' information may be used to generate the user's performance metrics or the performance level.

Figure 3C:
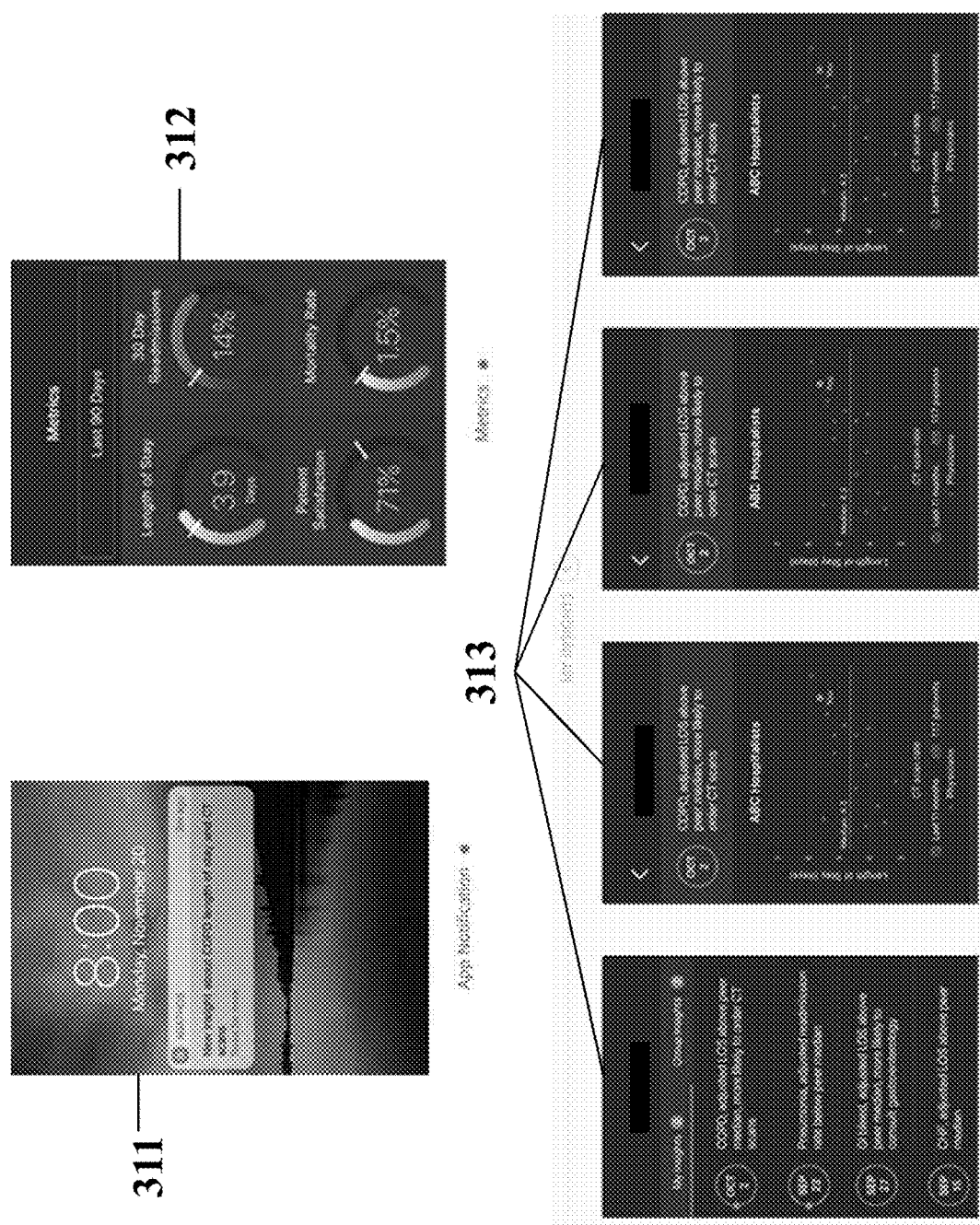
Figure 3D:
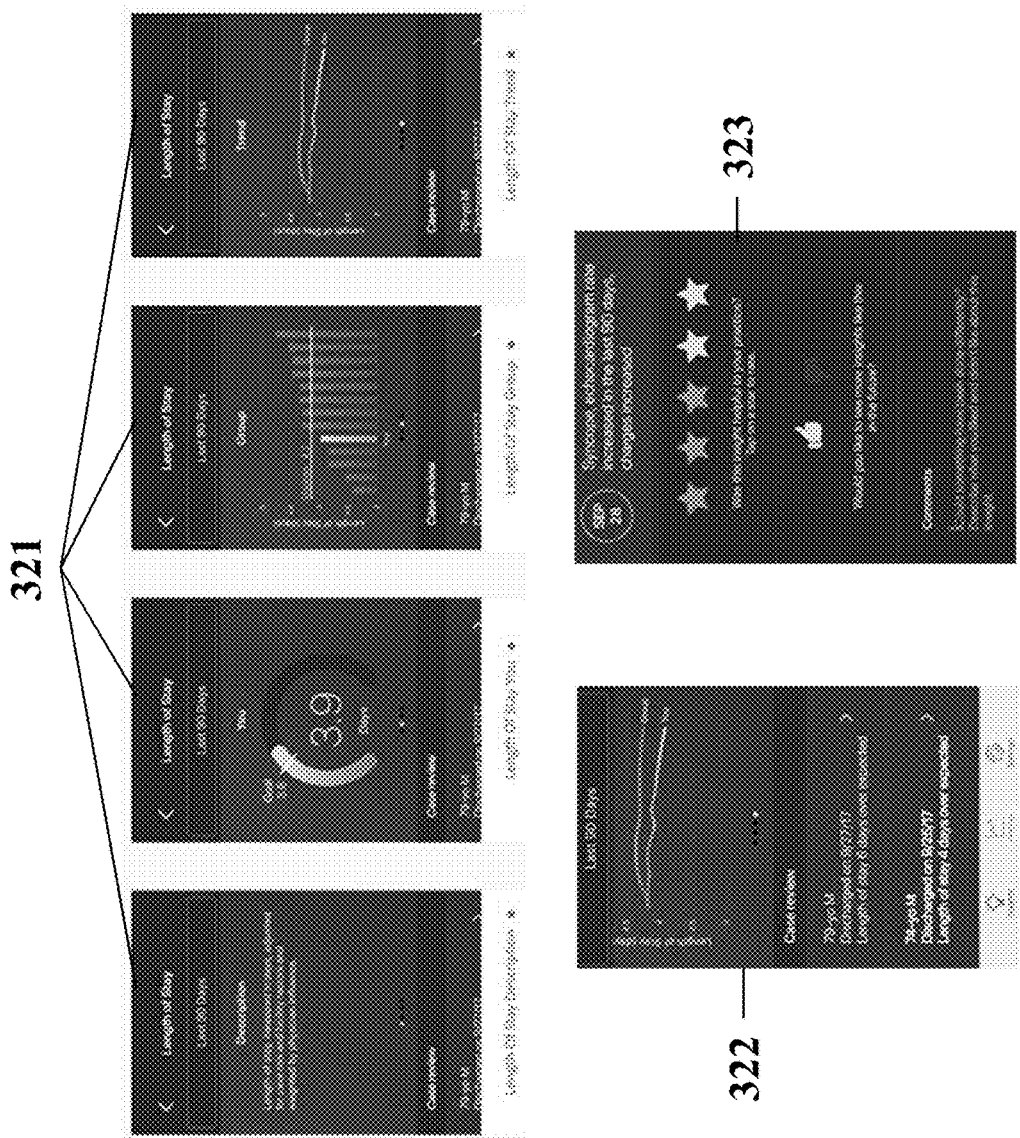

FIG. 3C comprises a plurality of UIs on a mobile electronic device of the user associated with an application of the system. In the illustrated example, the UI 311 shows a notification bar associated with the application. Personalized information such as performance metrics and insights may be dynamically provided to the user on the user interface. The notification bar may notify the user when new performance levels are available. In the illustrated example, the UI 312 shows a metrics screen of the application. The metrics screen may comprise a plurality of icons. The shape of the icons may be circle or any other shapes. Each of the icons may represent a description of a performance metric. The descriptions of the performance metrics may be length of stay, 30 days readmission, patient satisfaction, or mortality rate. The icons may be positioned at the top of the screen, the middle of the screen, the bottom of the screen, or a location that when a user is holding the device, all graphical elements are within reach of the user's thumb. In the illustrated example, the UIs 313 show a plurality of performance levels screens of the application. The performance levels screen may provide the user with the user's performance levels and the group's performance levels. The user's performance levels may include updates of the user's performance metrics and/or the user's action adjustment. The group's performance levels may inform the user about his/her performance metrics compared with group's performance metrics FIG. 3D comprises another set of UIs on the mobile electronic device of the user. In the illustrated example, UIs 321 show a plurality of length of stay screens of the application. The length-of-stay screens may provide the user with information about one or more user's patients' length of stay. The length-of-stay screens may provide the user with information about one or more group's patients' length of stay. The length-of-stay screens may also inform the user the comparison of the user's patients' length of stay and the group's patents' length of stay. The length-of-stay screens may show the trend of the user's patents' length of stay over a period of time, as demonstrated in UI 322. The period of time may be one day, one week, one month, one quarter, or longer. The UI 323 may notify the user about updates of his/her performance metrics and/or action adjustment.

Figure 3E:
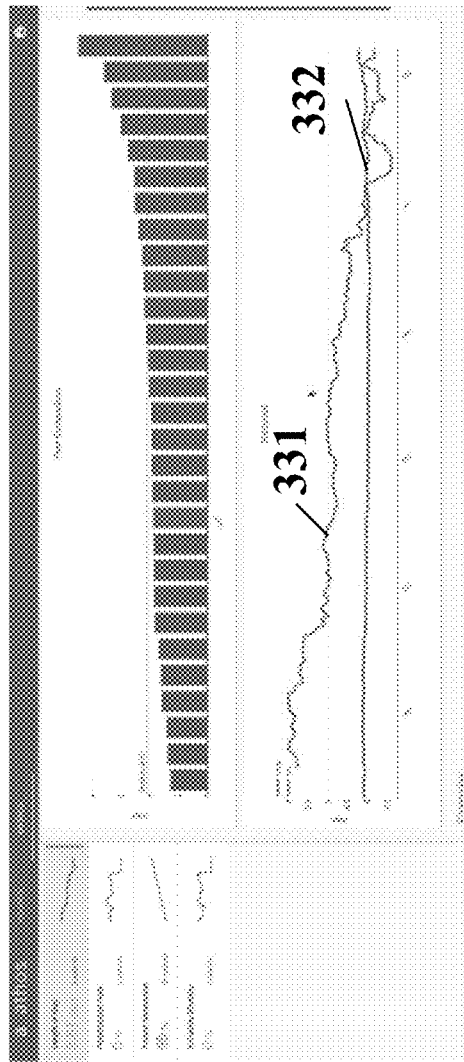
FIGS. 3E-3F show examples of web-based UIs.
Figure 3F:
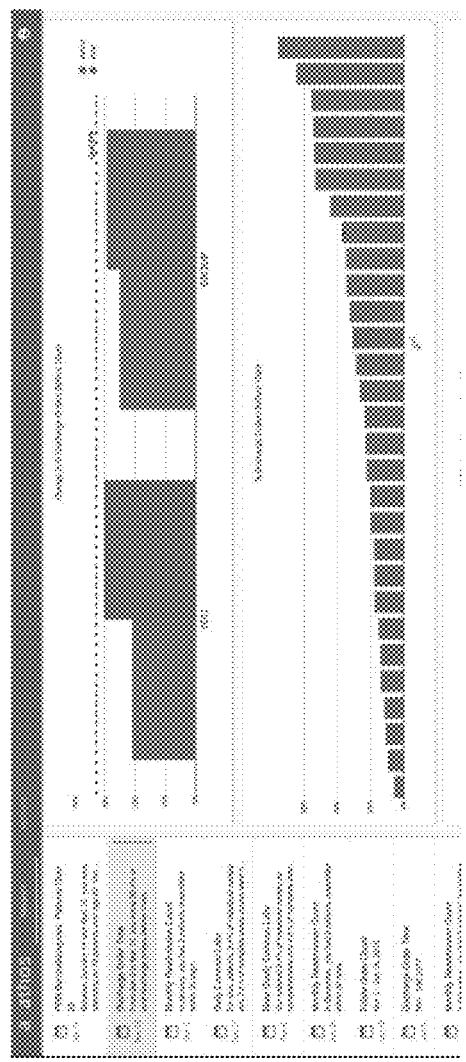

FIGS. 3E-3F illustrate examples of UIs in a software or a web browser. In the illustrated example, a plurality of metrics can be selected and/or shown on the UI. For example, length of stay, readmission rate, patient satisfaction, and in-facility mortality may be provided. One or more metrics of the user may be compared to a group as shown in the diagrams. For instance, the length-of-stay diagram shows the user's metric 331 in comparison of an average of the group's metric 332. FIG. 3F illustrates examples of a plurality of insights provided on a GUI. As described above, the insights are personalized and tailored to the specific user. In the example, various insights may be automatically generated and provided to the user. In some instances, at least some of the insights comprise actions suggested to be taken by the user. Such insights may comprise actionable feedback to the user in addition to non-actionable performance metrics. In some cases, notifications or messages of reminding the user to take certain actions may be delivered during a predefined time period, at one or more points in time, or at predetermined frequency. Such time period, time points or frequency may be automatically generated by the algorithms described elsewhere herein.

Figure 4:
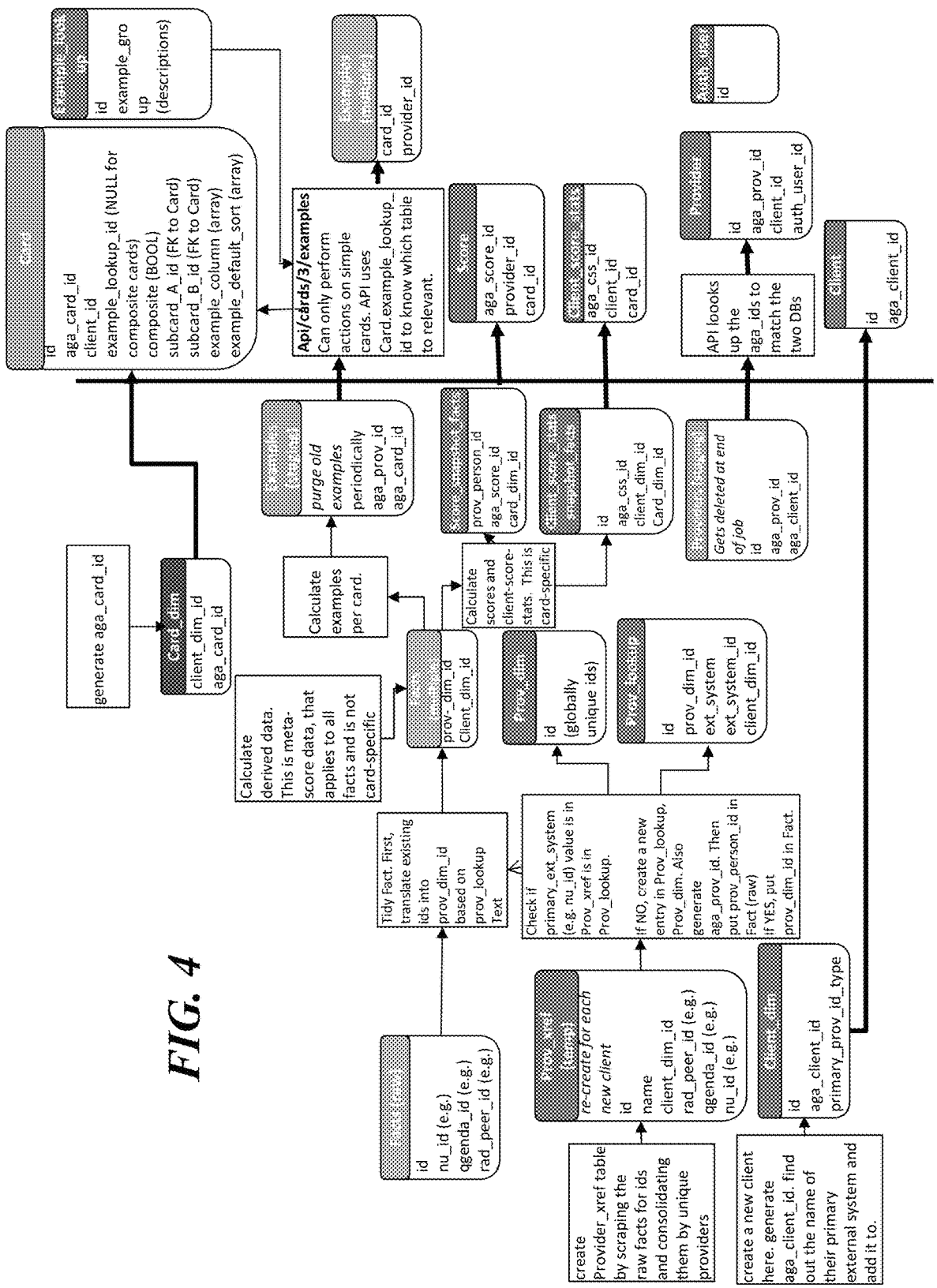
FIG. 4 shows an example of a network flow and data structures for use in a system described herein.

FIG. 4 shows examples data structures and network flow of the provided system. As shown in FIG. 4, the system may utilize pre-defined data scheme to record data related to a patient, a provider, and various other data as described elsewhere herein. For instance, a client table may be automatically created that may include client id, primary provider id type and other information. The provided system may be capable of auto-processing the various data and transform the data into the pre-defined structures such that the data can be suitable for processing by a machine learning algorithm trained model as described above.

Computer Systems

Figure 5:
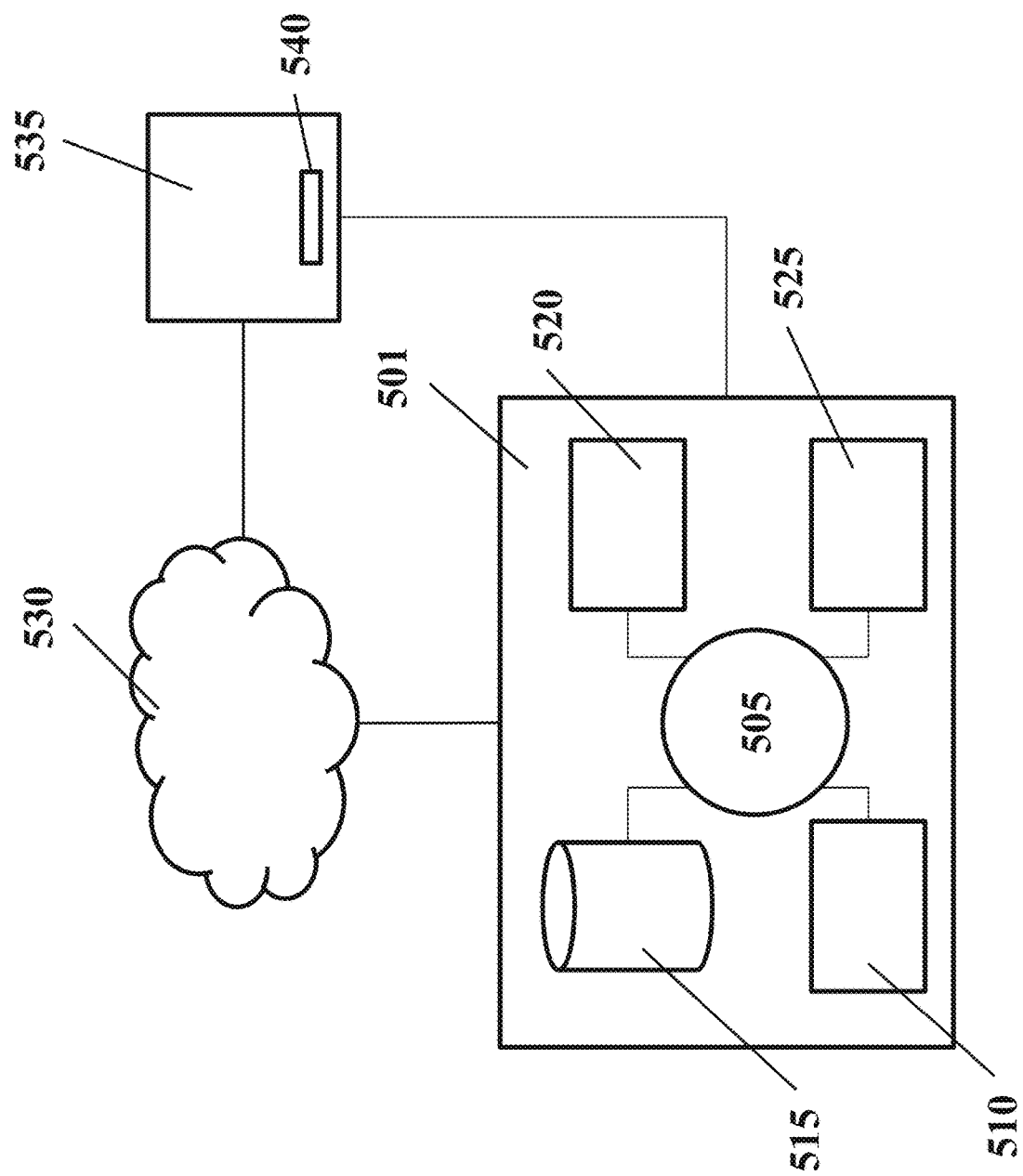
FIG. 5 shows a computer control system that is programmed or otherwise configured to implement methods provided herein.

The present disclosure provides computer systems that are programmed to implement methods of the disclosure. FIG. 5 shows a computer system 501 that is programmed or otherwise configured to implement the system for clinical care performance tracking and management. The computer system 501 can regulate various aspects of the system of the present disclosure, such as, for example, the machine learning process. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. Such cloud computing may be provided by cloud computing platforms such as, for example, Amazon Web Services (AWS) (AWS 202A in FIG. 2A), virtual private cloud (VPC 202B in FIG. 2A), Microsoft Azure, Google Cloud Platform, and IBM cloud. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface 540 for providing, for example, performance levels to the users. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for providing real-time actionable feedback personalized to individual clinical care providers, the system comprising:
   (a) a plurality of client devices, wherein each individual client device is configured to display a graphical user interface associated with a clinical care provider; and
   (b) a server in communication with the plurality of client devices and a database, wherein the server comprises: a first module configured to:
       (i) transform raw clinical care data into predefined tiered data structures and store the transformed clinical care data in the database, wherein the predefined tiered data structures are suitable for being processed by a feature extraction or feature selection technique,
       (ii) process the transformed clinical care data using a machine learning algorithm trained model to identify one or more performance metrics from a plurality of performance metrics to be one or more key performance metrics that impact a clinical care outcome in a selected field, and
       (iii) implement an influence algorithm to identify one or more actions that influence the one or more key performance metrics, wherein the one or more actions are used to personalize a notification for a selected clinical care provider to increase a likelihood of an adjustment of the one or more actions, and wherein implementing the influence algorithm comprises at least processing the transformed clinical care data in the predefined tiered data structures using the feature extraction or feature selection technique to assess an impact of the one or more actions on the one or more key performance metrics;

a second module configured to generate a real-time measurement of the one or more key performance metrics of the selected clinical care provider by computing a variation of the one or more key performance metrics of the selected clinical care provider relative to the one or more key performance metrics of a group of clinical care providers; and
   a third module configured to:
       (i) upon generation of the real-time measurement of the one or more key performance metrics of the selected clinical care provider, dynamically display on the graphical user interface of a client device of the selected clinical care provider the real-time measurement of the one or more key performance metrics of the selected clinical care provider,
       (ii) determine an adjustment of the one or more actions identified by the first module for the selected clinical care provider, wherein the adjustment is personalized for the selected clinical care provider based at least in part on the real-time measurement, and
       (iii) determine, based at least in part on a response of the selected clinical care provider to a previous notification, one or more points in time, a frequency or a time period to deliver a next notification to the client device of the selected clinical care provider to remind the selected clinical care provider to take the adjustment of the one or more actions thereby improving an engagement of the selected clinical care provider to the adjustment.

2. The system of claim 1, wherein the one or more key performance metrics comprise at least one of cost and quality.

3. The system of claim 1, wherein the machine learning algorithm trained model is configured to identify an attribution of a given action.

4. The system of claim 1, wherein the adjustment of the one or more actions is dynamically calculated based on the tracked behavior of the clinical care provider.

5. The system of claim 1, wherein the one or more key performance metrics in the selected field are different from one or more key performance metrics in a different field.

6. The system of claim 1, wherein the one or more key performance metrics comprise at least one of length of stay and readmission rate.

7. The system of claim 1, wherein the adjustment is further personalized based on the response of the selected clinical care provider to the previous notification.

8. The system of claim 1, wherein the tiered data structures comprise a top tier, a middle tier or a lower tier.

9. The system of claim 1, wherein the influence algorithm is further improved based on feedback collected from the selected clinical care provider.

10. A computer-implemented method for providing real-time actionable feedback personalized to individual clinical care providers, the method comprising:
   (a) transforming raw clinical care data into predefined tiered data structures and storing the transformed clinical care data in a database, wherein the predefined tiered data structures are suitable for being processed by a feature extraction or feature selection technique;
   (b) processing the transformed clinical care data using a machine learning algorithm trained model to identify one or more performance metrics from a plurality of performance metrics to be one or more key performance metrics that impact a clinical care outcome in a selected field;

(c) generating a real-time measurement of the one or more key performance metrics of the selected clinical care provider by computing a variation of the one or more key performance metrics of the selected clinical care provider relative to the one or more key performance metrics of a group of clinical care providers;

(d) implementing an influence algorithm to identify one or more actions that influence the one or more key performance metrics of the selected clinical care provider, wherein the one or more actions are used to personalize a notification for the selected clinical care provider to increase a likelihood of an adjustment of the one or more actions, and wherein implementing the influence algorithm comprises at least processing the transformed clinical care data in the predefined tiered data structures using the feature extraction or feature selection technique to assess an impact of the one or more actions on the one or more key performance metrics;

(e) dynamically displaying on a graphical user interface of a client device of the selected clinical care provider the real-time measurement generated in (c);

(f) determining an adjustment of the one or more actions identified in (d), wherein the adjustment is personalized for the selected clinical care provider based at least in part on the real-time measurement generated in (c); and (g) determining, based at least in part on a response of the selected clinical care provider to a previous notification, one or more points in time, a frequency or a time period to deliver a next notification to the client device of the selected clinical care provider to remind the selected clinical care provider to take the adjustment of the one or more actions thereby improving an engagement of the selected clinical care provider to the adjustment.

11. The computed-implemented method of claim 10, wherein the adjustment is further personalized based on the response of the selected clinical care provider to the previous notification.

12. The computed-implemented method of claim 10, further comprising improving the influence algorithm based on feedback collected from the selected clinical care provider.

13. The computed-implemented method of claim 10, wherein the tiered data structures comprise a top tier, a middle tier or a lower tier.

* * * * *